US009005398B2

(12) United States Patent
Brungardt

(10) Patent No.: US 9,005,398 B2
(45) Date of Patent: Apr. 14, 2015

(54) COMPOSITION AND USE OF HYDROGENATED ALKYL KETENE DIMERS

(71) Applicant: Hercules Incorporated, Wilmington, DE (US)

(72) Inventor: Clement L. Brungardt, Oxford, PA (US)

(73) Assignee: Solenis Technologies, L.P., Schaffhausen (CH)

( * ) Notice: Subject to any disclaimer, the term of this patent is extended or adjusted under 35 U.S.C. 154(b) by 0 days.

(21) Appl. No.: 14/060,921

(22) Filed: Oct. 23, 2013

(65) Prior Publication Data

US 2014/0174682 A1    Jun. 26, 2014

Related U.S. Application Data

(60) Provisional application No. 61/723,960, filed on Nov. 8, 2012.

(51) Int. Cl.

| | | |
|---|---|---|
| *D21H 17/53* | (2006.01) | |
| *D21H 17/17* | (2006.01) | |
| *A61K 31/365* | (2006.01) | |
| *C07C 49/88* | (2006.01) | |
| *C07D 305/12* | (2006.01) | |
| *D21H 19/18* | (2006.01) | |
| *D21H 19/44* | (2006.01) | |
| *D21H 19/46* | (2006.01) | |

(52) U.S. Cl.
CPC .............. *D21H 17/17* (2013.01); *A61K 31/365* (2013.01); *C07C 49/88* (2013.01); *C07D 305/12* (2013.01); *D21H 19/18* (2013.01); *D21H 19/44* (2013.01); *D21H 19/46* (2013.01)

(58) Field of Classification Search
USPC ................... 162/164.7, 158, 172, 164.1, 168; 549/263; 524/109
See application file for complete search history.

(56) References Cited

U.S. PATENT DOCUMENTS

| | | | |
|---|---|---|---|
| 2,614,922 A | 11/1947 | Hope | |
| 2,703,754 A | 3/1955 | Myers | |
| 2,859,110 A | 11/1958 | Sanford | |
| 2,959,513 A | 11/1960 | Savage | |
| 3,021,252 A | 2/1962 | Hill et al. | |
| 3,055,791 A | 9/1962 | Elias | |
| 3,058,871 A | 10/1962 | Davis et al. | |
| 3,629,171 A | 12/1971 | Kremer | |
| 3,822,178 A | 7/1974 | von Koppen et al. | |
| 5,539,035 A | 7/1996 | Fuller et al. | |
| 5,685,815 A | 11/1997 | Bottorff et al. | |
| 6,175,022 B1 | 1/2001 | Brungardt et al. | |
| 6,207,258 B1 | 3/2001 | Varnell | |
| 6,273,993 B1 | 8/2001 | Michelman | |
| 6,416,620 B1 | 7/2002 | Narancic et al. | |
| 6,811,824 B2 | 11/2004 | Hassan et al. | |
| 2006/0258620 A1 | 11/2006 | Smith et al. | |
| 2008/0020947 A1* | 1/2008 | Park et al. | 507/101 |
| 2011/0196027 A1* | 8/2011 | Sieber et al. | 514/449 |

FOREIGN PATENT DOCUMENTS

WO    9964934    12/1999

OTHER PUBLICATIONS

CN 103319325, machine translation, Sep. 2013.*
CN 103319325, machine translation, claims, Sep. 2013.*
E. L. Back, "Autodispersible waxes for recyclable packaging papers," Tappi Journal 78, No. 7, 161-168, 1995.
E. L. Back, "H2-Dimer," Tappi Journal 74, No. 4, pp. 37 & 39, 1995.
International Search Report, PCT/US2013/066339, Jan. 31, 2014, pp. 2.
"RN 2-oxetanone, 4-heptadecyl-3-hexadecyl", Chemical Abstracts Service, Jan. 25, 2006.

* cited by examiner

*Primary Examiner* — Mark Halpern

(74) *Attorney, Agent, or Firm* — Joanne Rossi; Michael Herman

(57) ABSTRACT

Latent dispersants were made by the hydrogenation of an alkyl ketene dimer, alkenyl ketene dimer, or ketene multimer. Adding the latent dispersant to paper or paperboard increased its resistance to water and water vapor while maintaining recyclability and repulpability. Additionally, provided is a method for increasing the repulpability of a wax coated paper or paperboard. Dispersants made by the hydrolysis of the alkyl ketene dimer, alkenyl ketene dimer, and ketene multimer are also described.

11 Claims, 5 Drawing Sheets

Structure of Hydrogenated Ketene Dimer (H$_2$-AKD)

Structure of Hydrolyzed, Hydrogenated Ketene Dimer

COMPOSITION AND USE OF HYDROGENATED ALKYL KETENE DIMERS

This application claims the benefit of U.S. provisional application No. 61/723,960, filed 8 Nov. 2012, the entire contents of which are hereby incorporated by reference.

BACKGROUND OF THE INVENTION

The presently disclosed and claimed inventive concepts relate to a composition for use in paper or paperboard applications. More specifically, the presently disclosed and claimed inventive concepts relate to a composition made by the hydrogenation or partial hydrogenation of an alkyl ketene dimer, alkenyl ketene dimer, or ketene multimer (collectively labeled $H_2$-AKD). The presently disclosed and claimed inventive concepts also relate to a composition that when mixed with pulp or applied as a coating to paper or paperboard, increases the water and water vapor resistance of the paper and paperboard while maintaining good recyclability and repulpability.

Paper products are frequently sized or coated in order to form a barrier against gases such as moisture vapor and liquids such as water, oils, and greases. Wax coated paper and paperboard are widely used to protect fresh fruit, vegetables, fish, and poultry during storage and shipping. In addition to acting as a barrier, the coating also strengthens and stiffens the paper or paperboard under wet or humid storage conditions.

The wax coating formulations applied to paper and paperboard are well known in the pulp and paper industry. Coating waxes typically have hydrocarbon chains containing from about 20 to about 40 carbon atoms and melting points of from about 40 degrees Celsius (° C.) to about 85° C. Paraffin and microcrystalline waxes are two such waxes commonly used in coated paper and paperboard applications. Typical examples of such materials include natural and/or synthetic waxes as set forth, for instance, in U.S. Pat. No. 3,058,871 (Davis et al.); U.S. Pat. No. 2,859,110 (Sanford) and U.S. Pat. No. 3,021,252 (Hill et al.).

There are four commonly used methods of applying wax coatings to paper and paperboard. One method for coating at low wax addition levels (less than 5% by weight) uses a pre-made aqueous wax emulsion. The wax emulsion can be added to the wet-end of the paper machine, on a size press, or on an off-machine coater. In the other three methods, curtain coating, wax impregnation, and cascade coating, the coating is typically applied as a molten wax at addition levels of at least 3% by weight of the coated board. A curtain coater applies a thin layer of wax onto one side of the paper or paperboard.

Typical addition levels range from about 5% to about 15% wax based on the total weight of the coated paper or paper board. Wax impregnated paper or paperboard is made by passing the paperboard through a nip flooded with molten wax. Due to its low surface tension and the pressure applied in the nip, the wax penetrates evenly throughout the paper or paperboard. Wax addition levels for impregnated paper or paperboard range from about 12% to about 20% of the total weight of the coated paper or paperboard. Cascade wax coatings are applied to cut, glued, finished sections of corrugated paperboard (e.g. combined liner/corrugated medium/liner). A section of corrugated paperboard is passed under a stream of molten wax, completely coating the flutes and outside surfaces of the paperboard. Wax addition levels for cascade coatings can range from about 20% to about 50% of the total weight of the coated paper or paperboard.

It has generally been found that the waxes present on, and impregnated in, coated paper and paperboard are difficult to separate effectively without contaminating the pulp and the paper-making machinery. During repulping, the molten or semi-molten wax clings to the pulp fibers and repulping equipment. If it is not separated from the pulp fibers, the residual wax forms defects in the recycled paper or paperboard and deposits on the paper machine. Therefore, wax coated boxes cannot be recycled; they must be separated from recyclable boxes and either burned or used as landfill thereby increasing handling costs and creating environmental concerns.

A number of methods of removing wax from recycled paper and paperboard have been proposed. U.S. Pat. No. 3,058,871 (Davis, et. al.) and U.S. Pat. No. 2,703,754 (Myers) disclose the separation of hot melt coatings from the pulp by solvent extraction of the coating. Additionally, Myers teaches the separation of pulp and coating material as made by a combination of emulsification and solvent extraction. In U.S. Pat. No. 3,055,791 (Elias), solid absorbants are used in an attempt to recover pulp, whereas in U.S. Pat. No. 3,021,252 (Hill, et. al.) and U.S. Pat. No. 2,859,110 (Sanford), the coating is mechanically separated from the fiber. U.S. Pat. No. 3,822,178 (von Koeppen, et. al.); U.S. Pat. No. 2,614,922 (Hope); U.S. Pat. No. 2,859,110 (Sanford); and U.S. Pat. No. 2,959,513 (Savage), disclose procedures for recycling wax coated paper involving suspending the coating particles in a hot aqueous system. All of the above referenced patents are hereby incorporated herein by reference.

It has also been suggested that the addition of dispersants during repulping can improve the removal of wax by mechanical methods. However, these approaches are not economically feasible as the process requires treatment of the entire recycled pulp furnish with expensive chemical additives regardless of the amount of wax present.

While some of these methods have been commercially successful, a more general solution that can be adopted by the paper industry with minimal capital investment is needed. The use of fatty acids, and other organic carboxylic acids, in wax coatings for paper and paperboard is disclosed in U.S. Pat. No. 3,629,171 (Kremer). More recently, E. L. Back, "Corrugated Paperboard Project Researches Self-Dispersing Wax," Tappi Journal, volume 74, no. 4, pages 37-38, July 1992; J. Michelman, "Method of Dispersing Wax from a Hot Melt Wax-coated Paper," U.S. Pat. No. 6,273,993, Aug. 14, 2001; and Fuller et al., "Recyclable Wax-coated Container," U.S. Pat. No. 5,539,035, Jul. 23, 1996; proposed incorporating a fatty acid or other dispersant into the wax coating formulation to simplify repulping and recycling.

U.S. patent application Ser. No. 07/907,173 (Michelman) describes the addition of a "latent dispersant" to wax coatings. Fuller et al., "Recyclable wax-coated container," U.S. Pat. No. 5,539,035, Jul. 23, 1996, describe repulpable wax coatings made from mixtures of paraffin wax, fatty acid, and a compatible hydrophobic polymer additive such as polyethylene propylene rubber. Hassan et al., "Repulpable wax," U.S. Pat. No. 6,811,824, Nov. 2, 2004, disclose repulpable water resistant coatings for paper and paperboard based on hydrogenated triglyceride fatty acid esters.

Narancic et al., "Method of Repulping Repulpable and Recyclable Moisture Resistant Coated Articles," U.S. Pat. No. 6,416,620, Jul. 9, 2002, describe the addition of inorganic mineral fillers to improve the repulpability of wax coatings. Narancic, et al. teach that the addition of a fatty acid or surfactant to a wax coating can cause corrosion problems on handling equipment and reduce the coating's resistance to water and water vapor.

Ideally, a repulping additive for wax coatings should be physically compatible with wax over a wide range of addition levels. To simplify handling, it should have a melting point close to that of commercial wax coatings. Additionally, the additive should not negatively affect the water and water vapor resistance of the wax coating. The resulting repulpable wax coating should maintain its water and water vapor resistance for long periods of time under the wet (neutral pH), humid, and high temperature conditions encountered during the storage and shipping of produce. For example, standard "tropical" moisture vapor transmission rate (MVTR) testing of wax coated paperboard is carried out at about 38° C. and 90% relative humidity. Also, the ideal wax repulping additive should be based on renewable raw materials.

For recycling purposes, the wax coated paper or paperboard should be repulpable under pH and temperature conditions readily available to the paper maker without large capital investment. To minimize deposition on repulping equipment, the wax coated paper or paperboard should be repulpable at temperatures below the melting point of the wax. Finally, any additive and/or wax should not cause corrosion problems on the coating, repulping, or paper making equipment.

The hydrogenated alkyl ketene dimer, alkenyl ketene dimer, or ketene multimer (collectively identified as $H_2$-AKD) of the current composition offer several advantages over the related art. The fatty acids, anionic surfactants, and cationic surfactants described by Back, Michelman, and Fuller are hydrophilic salts under the neutral pH conditions encountered by wax coated paper and paperboard during storage and shipping. Similarly, the nonionic surfactants described in the prior art are hydrophilic and water miscible. Adding these hydrophilic materials inevitably reduces the water resistance of the wax coating. Because of the warm, humid conditions encountered during the shipping and storage of produce, it is unlikely that the coatings described by Hassan, which are comprised primarily of triglycerides, can resist microbial growth for long periods of time under these conditions.

By contrast, $H_2$-AKD is hydrophobic under end-use conditions and can be added directly to wax at the levels needed to improve repulpability without compromising the water and water vapor resistance of the coating. Additionally, since $H_2$-AKD is a non-polar hydrophobic wax, it is not corrosive to coating or paper making equipment.

As described below, $H_2$-AKD addition levels as low as 5% by weight of total coating can improve the repulpability of a wax coating. Also advantageous is that $H_2$-AKD is based on renewable, fatty acid raw materials.

Additional objects, advantages, and features of what is claimed will be set forth in the description that follows and in part will become apparent to those skilled in the art upon examination of the following or may be learned by the practice of the technology. The objects and advantages of the presently disclosed and claimed inventive concepts will be realized and attained by means of the compositions and methods particularly pointed out in the appended claims, including the functional equivalents thereof.

DETAILED DESCRIPTION

In accordance with the present invention, there are provided compositions comprising Formula I:

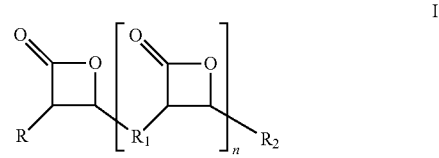

wherein
R is a branched or straight chain alkyl that is at least 6-carbon atoms in length;
$R_1$ is a branched or straight chain alkyl containing from 2 to 34 carbon atoms;
$R_2$ is a branched or straight chain alkyl that is at least 6-carbon atoms in length;
Wherein
R, $R_1$ and $R_2$ may independently, optionally contain a cyclic functional group; and
n is an integer from 0 to 6.

Therefore, in accordance with the invention, a latent dispersant with the generic structure shown in Formula I, is made by the hydrogenation of an alkyl ketene dimer, alkenyl ketene dimer, or ketene multimer (collectively identified as $H_2$-AKD). Alkyl ketene dimers, alkenyl ketene dimers, and ketene multimers that have not undergone hydrogenation, (collectively AKD's) are currently used as internal and surface sizing agents by the paper industry. A generic chemical structure for these starting materials can be found in U.S. Pat. No. 5,685,815 (Bottoroff). Other examples can be found in U.S. Pat. No. 6,175,022 (Brungardt) and U.S. Pat. No. 6,207,258 (Varnell), wherein carboxylic acids and dicarboxylic acids are used to make alkyl ketene dimers, alkenyl ketene dimers, and ketene multimers (AKD's).

Figure 1:
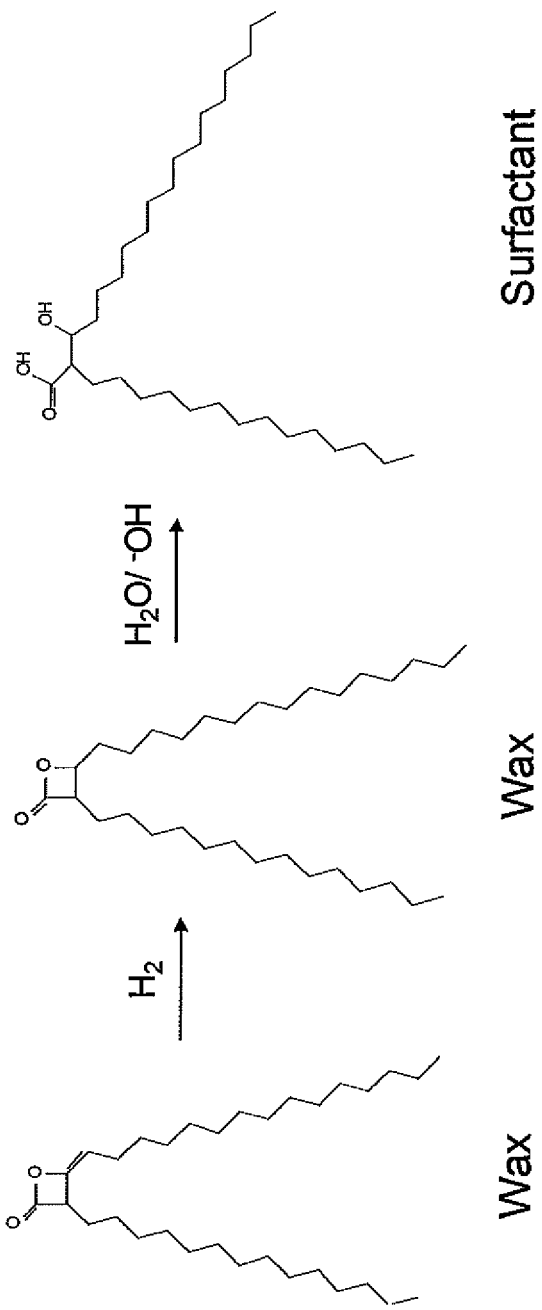
FIG. 1, illustrates one possible mechanism for the hydrogenation and hydrolysis of an alkyl ketene dimer.

The hydrogenation reaction acts to reduce the carbon-to-carbon double bond(s) attached to the four-membered lactone ring(s) of the alkyl ketene dimer, alkenyl ketene dimer, or ketene multimer (See FIG. 1). Hydrogenation also acts to reduce any carbon-to-carbon double bonds in the hydrocarbon chains attached to the lactone ring(s). A generic chemical structure for the resulting hydrogenated ketene dimer or ketene multimer is shown in Formula I, wherein "n" is from 0 to 6, can be 0 to 3 and may be 0. $R_1$ may contain 2 to 34 carbon atoms and may be a straight or a branched alkyl group, and may contain cyclic functional groups. R and $R_2$ are at least 6-carbon atoms in length; can contain 10 to about 22 carbons in length; can be from about 10 to about 20 carbons in length; and may be from about 12 to about 18 carbons in length. R and $R_2$, are selected from straight chain or branched alkyl groups and may also contain cyclic functional groups.

The carboxylic acids used to make the alkyl ketene dimer, alkenyl ketene dimer, or ketene multimer starting materials can contain other functional groups, such as, for example, esters, ethers, tertiary and quaternary amines, carbon-to-carbon double and triple bonds, ketones, aldehydes, aliphatic rings and aromatic rings and any functional groups as described in U.S. Pat. No. 6,175,022. It is also understood that the present invention also contains regio isomers of the compounds of Formula I. It is also understood that the present invention contains regio isomers of the compounds of Formula II.

What is meant by dispersant is a substance that aids in separating and dispersing small, insoluble particles of hydrophobic materials in a substantially aqueous environment. The dispersant can be used in combination with a chemical agent, such as $NaHCO_3$, $Na_2CO_3$, and NaOH, which are capable of modifying the carboxylic acid group(s) present on the dispersant.

A further objective is to provide a method of increasing the water and water vapor resistance of paper and paperboard while maintaining recyclability and repulpability. When added to paper or paperboard, or applied as a coating on the paper or paperboard, a composition comprising $H_2$-AKD, or partially hydrogenated $H_2$-AKD, increases the water and water vapor resistance of the paper or paperboard. Hereinafter, when referring to $H_2$-AKD, it is understood that this can mean a partially hydrogenated AKD. The $H_2$-AKD remains a hydrophobic wax under normal end-use, storage, and shipping conditions. When the $H_2$-AKD treated paper or paperboard is exposed to hot water and alkaline conditions during recycling or repulping, it is believed to react to form an anionic soap. The anionic soap can then be dispersed in water and separated from the cellulose pulp.

Figure 2:
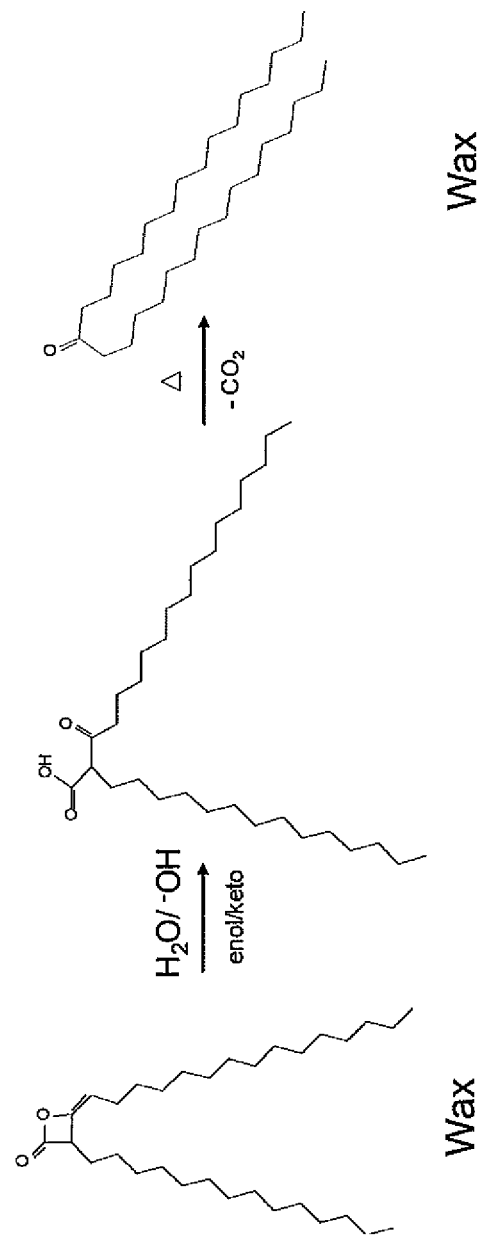
FIG. 2, illustrates one possible alkyl ketene dimer hydrolysis mechanism.
Figure 3:
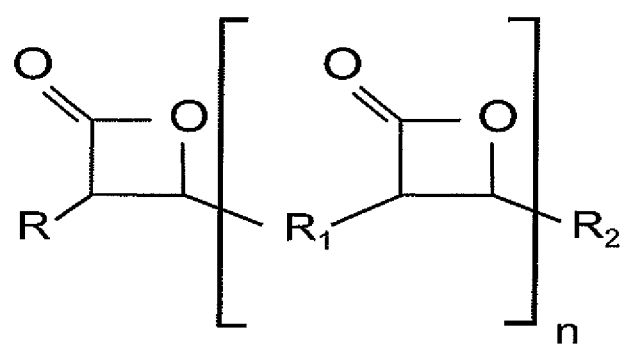
FIG. 3, illustrates a generic chemical structure for the resulting hydrogenated ketene dimer or ketene multimer.
Figure 4:
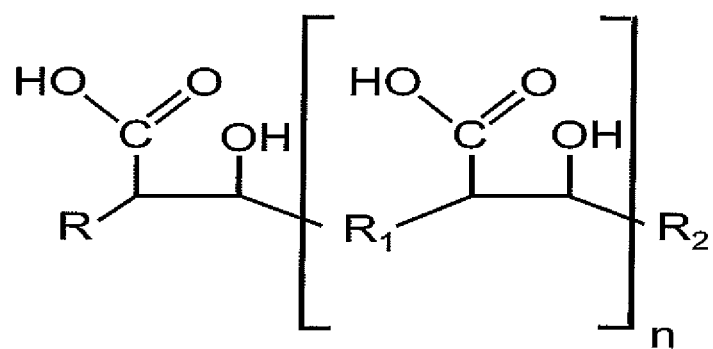
FIG. 4, illustrates a generic chemical structure for hydrolyzed, hydrogenated alkyl ketene dimer, alkenyl ketene dimer, or ketene multimer.

One possible mechanism for the improved repulpability obtained with $H_2$-AKD is illustrated in FIG. 1 and FIG. 2. Commercially available AKD reacts with water to form a beta-keto carboxylic acid. The beta-keto carboxylic acid loses $CO_2$ rapidly at room temperature to form a waxy, hydrophobic ketone. This waxy ketone would not be expected to improve the repulpability of a wax coating. However, hydrogenation of AKD yields a hydrophobic wax with a reactive lactone ring. The lactone ring can undergo hydrolysis during repulping to form stable carboxylic acid soap. The anionic soap can be easily dispersed in water and separated from the cellulose pulp.

A generic chemical structure for the hydrolyzed analogue of the hydrogenated alkyl ketene dimer, alkenyl ketene dimer, or ketene multimer is given in Formula II.

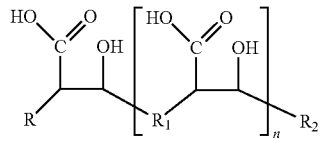

II wherein

R is a branched or straight chain alkyl that is at least 6-carbon atoms in length;

$R_1$ is a branched or straight chain alkyl containing from 2 to 34 carbon atoms;

$R_2$ is a branched or straight chain alkyl that is at least 6-carbon atoms in length;

Wherein

R, $R_1$ and $R_2$ may independently, optionally contain a cyclic functional group; and n is an integer from 0 to 6.

In Formula II, "n" can be from 0 to 6; can be 0 to 3; and may be 0. R and $R_2$, are selected from straight chain or branched alkyl groups, and may also independently contain cyclic functional groups. R and $R_2$ are at least 6-carbon atoms in length; can contain 10 to about 22 carbons in length; can be from about 10 to about 20 carbons in length; and may be from about 12 to about 18 carbons in length. $R_1$ can contain 2 to 34 carbon atoms and may be a straight chain or branched alkyl group, and may optionally contain cyclic functional groups.

Alternatively, the $H_2$-AKD wax can be incorporated into a conventional wax coating. The hydrophobic hydrocarbon nature of $H_2$-AKD and its melting point (56° C.), make it compatible with conventional coating waxes. For example, Paraflex®4797A (The International Group, Agincourt, Ontario, Canada) has a melting point of 59° C. When the $H_2$-AKD/wax coated paper or paperboard is exposed to alkaline repulping conditions, an anionic soap formed from the $H_2$-AKD helps to disperse the conventional wax, making it easier to separate from the cellulose pulp.

The waxes that can be used with $H_2$-AKD to coat paper and paperboard are known in the art of papermaking and include: paraffin wax, microcrystalline wax, or any natural or synthetic wax coating compositions, but not limited to plant waxes, animal waxes and petroleum derived waxes. Commercial examples of such waxes are available from The International Group (Agincourt, Ontario, Canada). The waxes currently used to coat paper or paperboard typically contain from about 20 to about 40 carbon atoms in their hydrocarbon chains and have melting points from about 30° C. to about 200° C.; and can have melting points between about 40° C. and about 85° C. In addition to wax, the formulations may also include optional resins, such as thermoplastic polymeric materials, for example hydrocarbon resins, polyethylene vinylacetate, polyethylene and the like to enhance the physical properties of the coating, reduce cost and improve performance.

The $H_2$-AKD or the $H_2$-AKD/wax composition can be applied by any of the methods used to apply a coating of wax to paper or paperboard, including, for example, as an emulsion, on a curtain coater, on a wax impregnator or on a cascade coater. U.S. Pat. No. 4,317,756 (Dumas, et. al.), discloses methods for making aqueous emulsions of alkyl ketene dimer (AKD), which can then be used for making emulsions of the hydrogenated compositions of the present invention.

When added by itself or in combination with a conventional wax, the $H_2$-AKD/wax composition addition level can range from about 1% to about 60% of the total weight of the coated paper or paperboard. $H_2$-AKD can range from about 1% to about 100% by weight of the coating composition; can be from about 5% to about 50% by weight of the coating composition; and may be about 15% to about 25% by weight of the coating composition. It should be understood that throughout the specification and claims the term coating is understood to mean "coating" or "impregnation" unless otherwise indicated.

A further objective is to provide a method of increasing the repulpability of a coated paper or paperboard. Paper or paperboard coated with a $H_2$-AKD or $H_2$-AKD/wax composition can be repulped at a pH of from about 5 to about 14; can be repulped at a pH of from about 7 to about 12; and may be repulped at a pH of from about 9 to about 12.

Paper or paperboard coated with a $H_2$-AKD or $H_2$-AKD/wax composition can be repulped at temperatures of from about 20° C. to about 100° C.; can be repulped at temperatures of from about 30° C. to about 70° C.; and may be repulped at a temperature of from about 40° C. to about 60° C. The paper or paperboard coated with the $H_2$-AKD or $H_2$-AKD/wax composition may also be repulped at about 50° C.

While there is no rigid differentiation between paper and paperboard, paperboard is generally thicker (usually over 0.25 mm/0.010 in or 10 points) than paper. The present composition can be used with any paper or paperboard. Examples of paper and paperboard types and classification can be found in TAPPI Method—TIP 0404-36, which is herein incorporated in its entirety.

The following examples are intended to be illustrative of the presently disclosed and claimed inventive concepts. However, these examples are intended to be non-limiting embodiments of the invention.

EXAMPLES

The following examples are provided to illustrate the production and activity of representative compositions of the present teachings and to illustrate their water and water vapor resistance, and performance in recycling and repulping operations. One skilled in the art will appreciate that although specific reagents and conditions are outlined in the following examples, these reagents and conditions are not a limitation on the present teachings.

Example 1

Hydrogenation of Alkyl Ketene Dimer

A sample of Aquapel® 364, alkyl ketene dimer (AKD) (available from Ashland Water Technologies—Lexington, Ky.) was hydrogenated using the following method: 25 grams (g) of alkyl ketene dimer was dissolved in 25 g of toluene. The mixture was then loaded into a stainless steel Parr reactor along with 2 mole % of Pd catalyst on carbon (10% palladium on carbon, available from Aldrich—Milwaukee Wis.). The reactor was flushed two times with $H_2$ gas, sealed under 600 pounds per square inch of $H_2$ gas pressure, and then stirred for 18 hours at room temperature. Once the reaction was complete, the mixture was filtered to remove the Pd catalyst, and the toluene solvent was removed under vacuum. Twenty four grams of the desired $H_2$-AKD composition were isolated. The $H_2$-AKD composition had a melting point of 56° C.

Example 2

Preparation of Paperboard

Paperboard for wax coating was made using the following method. A sample of commercial paperboard was cut into 2.5 centimeter (cm) strips, then refined to a Canadian standard freeness (CSF) of 375 milliliter (mL) using a double disc refiner. 2.5 weight % of GPC™D-15F (Grain Processing Corporation—Muscatine, Iowa) was added to the refined pulp.

Recycled paperboard was made from the pulp furnish using a pilot paper machine similar to the one available at Western Michigan University in Kalamazoo, Mich. The temperature of the paper making pulp was set at 50° C. Paper making pH was fixed at 7.5. The following additives were added to the wet-end of the paper machine: 0.5 weight % Stalok®300 cationic starch (all addition levels based on pulp furnish, Tate and Lyle—London, United Kingdom), 0.05 weight % Hercon®70 alkyl ketene dimer sizing agent emulsion (Ashland Hercules Water Technologies—Lexington Ky.), and 0.0125 weight % Perform®8713 cationic polyacrylamide retention aid (Ashland Water Technologies—Lexington Ky.). Basis weight was fixed at 160 grams per meter squared (g/m²). Sheet moisture at the reel was controlled to 8%.

Example 3

Preparation of Wax Coated Paperboard

The recycled paperboard made in Example 2 was coated with Paraflex®4797A wax using the following method (a commercial cascade wax supplied by the International Group). A 200 g sample of Paraflex®4797A was melted using a hot water bath set at 80° C. The recycled paperboard was cut into 6 inch×6 inch squares. The squares were then dipped into the molten wax for 5 seconds, removed, and allowed to cool at room temperature for one hour. Paraflex®4797A coatings containing 5%, 10%, 15%, 25%, 50% and 100% $H_2$-AKD were also made by the same method. The $H_2$-AKD was made using the method described in Example 1. The coated samples were cured in an oven at 85° C. for 30 minutes prior to testing. Wax pick-up averaged 50% of the total weight of the coated paperboard.

Example 4

Repulpability Test Method

The repulpability of the uncoated paperboard, the Paraflex®4797A coated paperboard, $H_2$-AKD coated paperboard, and $H_2$-AKD/wax coated paperboard described in Example 3 were measured using the following method.

A 342 g aliquot of water was placed into a Waring Blender. An 18 g sample of paperboard was cut into 2.5 cm×2.5 cm squares and placed into the blender. An electric motor fitted to the bottom of the blender was used to rotate the blade. The blade was rotated in a "reverse" direction, to avoid cutting the pulp with the sharp edge of the blade. Stirring rate was fixed at 1500 revolutions per minute (rpm). A 1N solution of sulfuric acid ($H_2SO_4$) was used to adjust the repulping dispersion to pH 5. $NaHCO_3$ (1000 ppm) was used to buffer the repulping dispersion to pH 7. $Na_2CO_3$ (1000 ppm) was used to buffer the repulping dispersion to pH 9, and a mixture of $Na_2CO_3$ (1000 ppm) and NaOH was used to buffer the repulping dispersion to pH 12. Water temperature was controlled using an electric heating jacket wrapped around the outside of the blender.

Figure 5:
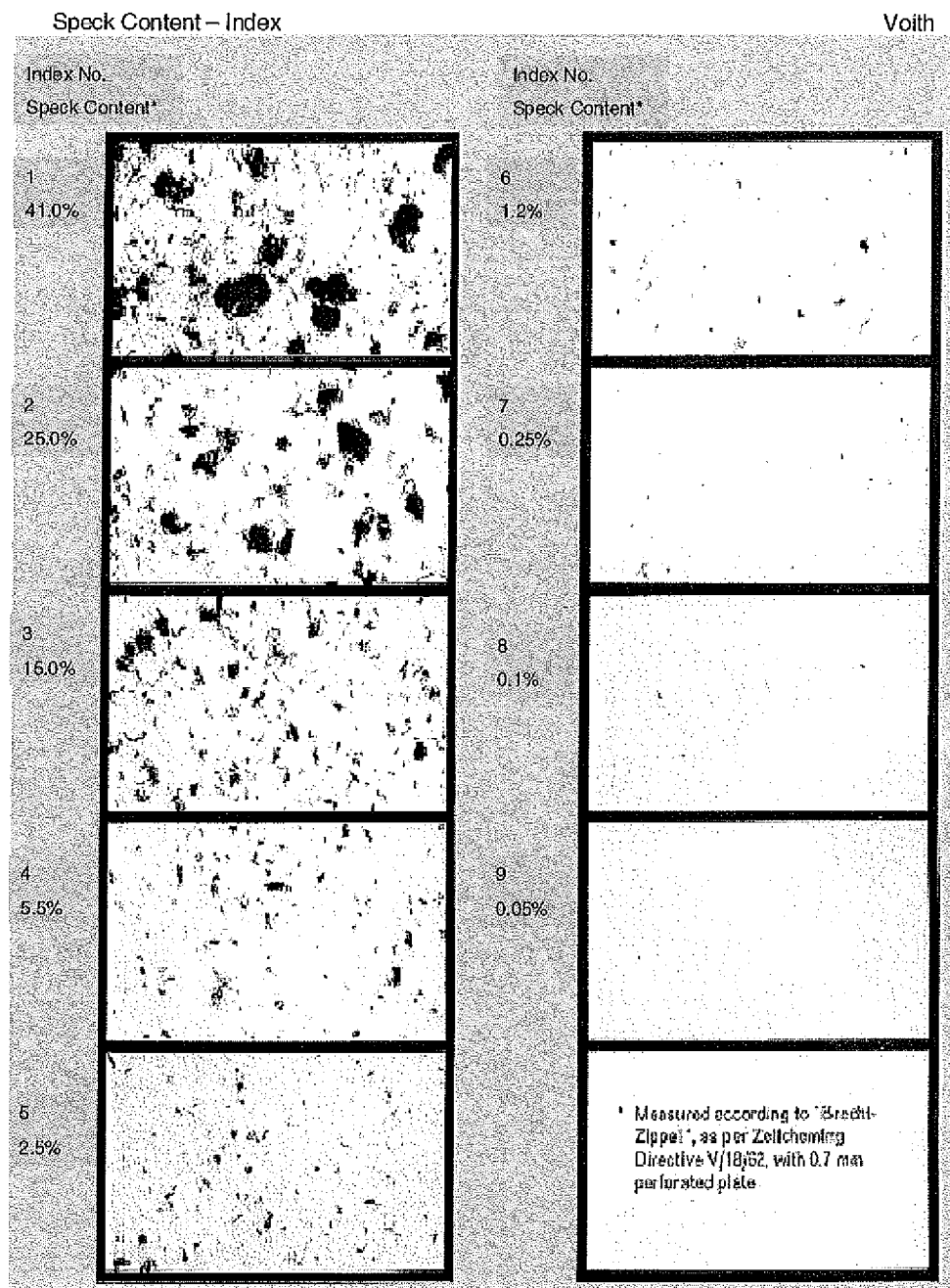
FIG. 5, illustrates various degrees of repulping that was quantified by comparing each sample to a series of repulping standards.

Samples of the pulp slurry were taken every 15 minutes. The degree of repulping was quantified by comparing each sample to the series of repulping standards shown in FIG. 5. A repulping index value of "5" is considered to be acceptable for commercial use.

Example 5

Repulpability of Various Wax/$H_2$-AKD Blends

Samples of Parallex®4797A, $H_2$-AKD, and Paraflex®4797A/$H_2$-AKD coated paperboard were made using the methods described in Examples 2 and 3. Total wax pick-ups averaged 50% of the weight of the coated paperboard. Repulpability was measured at pH's ranging from 5 to 12, at repulping temperatures of 40° C., 50° C., and 60° C. using the method described in Example 4 (See Tables 1-3).

The 100% Paraflex®4797A wax coated paperboard repulped slowly at temperatures below its melting point of 59° C. The highest repulping index value obtained for the 100% Paraflex®4797A wax coated paperboard was only 2.5 at repulping temperatures below its melting point (measured after two hours of repulping at 50° C. and pH 12). Increasing repulping temperature to 60° C., above the melting point of the wax, greatly increased the repulping rate of the 100%

Paraflex®4797A wax coated paperboard. However, wax becomes sticky and forms heavy deposits at repulping temperatures around its melting point resulting in operational issues.

Adding $H_2$-AKD to the Paraflex®4797A wax improved the repulpability of the wax coated board over the entire range of repulping pH's and temperatures tested.

The amount of improvement (versus 100% Paraflex®4797A wax) depended on the repulping pH and the percentage of $H_2$-AKD added to the wax. In general, the repulpability of the $H_2$-AKD or $H_2$-AKD/wax composition improved as pH increased from 5 to 12. At pH 12 and 50° C., the $H_2$-AKD/Paraflex 4797A compositions containing at least 15% $H_2$-AKD repulped quickly at temperatures below the wax melting point (repulping temperature of 50° C.). Improvements in repulpability were observed at $H_2$-AKD addition levels as low as about 5% to about 10% of the total wax coating. The repulpability of the $H_2$-AKD and $H_2$-AKD/wax coated paperboard also improved as the percentage of $H_2$-AKD in the coating increased. The 100% $H_2$-AKD coating repulped the most quickly. At pH 12, the 100% $H_2$-AKD coated paper board gave "acceptable" repulpability (Repulpability Index of at least "5") at temperatures as low as 40° C.

TABLE 1

Repulpability of Wax Coatings - 40° C.

| % H2 AKD | % Wax | \multicolumn{8}{c}{Repulping Time (Minutes)} | | | | | | | |
|---|---|---|---|---|---|---|---|---|---|
| | | 15 | 30 | 45 | 60 | 75 | 90 | 105 | 120 |
| \multicolumn{9}{c}{pH 7} | | | | | | | | |
| Blank | | 2 | 3.5 | 6 | 8 | N/A | N/A | N/A | N/A |
| 0 | 100 | 1 | 1 | 1 | 1 | 1.5 | 1.5 | 2 | 2 |
| 5 | 95 | 1 | 1 | 1 | 1 | 1.5 | 1.5 | 2 | 2 |
| 10 | 90 | 1 | 1 | 1 | 1 | 1.5 | 1.5 | 2 | 2 |
| 15 | 85 | 1 | 1 | 1 | 1.5 | 1.5 | 1.5 | 2 | 2 |
| 25 | 75 | 1 | 1 | 1.5 | 1.5 | 2 | 2 | 2 | 2 |
| 50 | 50 | 1 | 1.5 | 2 | 2 | 2.5 | 2.5 | 3 | 3 |
| 100 | 0 | 1 | 1.5 | 2 | 2 | 2 | 3 | 3 | 3 |
| \multicolumn{9}{c}{pH 9} | | | | | | | | |
| Blank | | 2 | 3 to 4 | 6 | 8 | N/A | N/A | N/A | N/A |
| 0 | 100 | 1 | 1 | 1 | 1 to 2 | 1 to 2 | 1 to 2 | 1 to 2 | 1 to 2 |
| 5 | 95 | 1 | 1 | 1 to 2 | 1 to 2 | 1 to 2 | 1 to 2 | 1 to 2 | 2 |
| 10 | 90 | 1 | 1 | 1 to 2 | 1 to 2 | 1 to 2 | 1 to 2 | 2 | 2 |
| 15 | 85 | 1 | 1 | 1 | 1 to 2 | 2 | 2 | 2 | 2 to 3 |
| 25 | 75 | 1 | 1 | 1 to 2 | 2 | 2 | 2 to 3 | 2 to 3 | 2 to 3 |
| 50 | 50 | 1 | 2 | 2 to 3 | 2 to 3 | 3 | 3 | 3 to 4 | 3 to 4 |
| 100 | 0 | 1 | 2 | 2 to 3 | 2 to 3 | 3 | 3 | 3 to 4 | 4 |
| \multicolumn{9}{c}{pH 12} | | | | | | | | |
| Blank | | 2 | 3 to 4 | 6 | 8 | N/A | N/A | N/A | N/A |
| 0 | 100 | 1 | 1 | 1 | 1 to 2 | 1 to 2 | 2 to 3 | 2 to 3 | 2 to 3 |
| 5 | 95 | 1 | 1 | 1 to 2 | 1 to 2 | 2 | 2 | 2 to 3 | 3 |
| 10 | 90 | 1 | 1 | 1 to 2 | 1 to 2 | 2 | 2 | 2 to 3 | 3 |
| 15 | 85 | 1 | 2 | 2 | 3 | 3 | 3 to 4 | 3 to 4 | 3 to 4 |
| 25 | 75 | 1 | 1 | 2 to 3 | 3 | 3 | 3 to 4 | 3 to 4 | 3 to 4 |
| 50 | 50 | 1 | 2 | 2 to 3 | 3 | 3 to 4 | 4 | 4 to 5 | 5 |
| 100 | 0 | 1 | 2 | 2 to 3 | 3 | 3 to 4 | 4 | 4 to 5 | 5 |

TABLE 2

Repulpability of Wax Coatings - 50° C.

| % H2 AKD | % Wax | \multicolumn{8}{c}{Repulping Time (Minutes)} | | | | | | | |
|---|---|---|---|---|---|---|---|---|---|
| | | 15 | 30 | 45 | 60 | 75 | 90 | 105 | 120 |
| \multicolumn{9}{c}{pH 5} | | | | | | | | |
| Blank | | 2 | 3 to 4 | 6 | 8 | N/A | N/A | N/A | N/A |
| 0 | 100 | 1 | 1 | 1 | 1 | 1 | 1 | 1 | 1 |
| 5 | 95 | 1 | 1 | 1 to 2 | 1 to 2 | 1 to 2 | 2 | 2 | 2 |
| 10 | 90 | 1 | 1 | 1 to 2 | 1 to 2 | 1 to 2 | 2 | 2 | 2 to 3 |
| 15 | 85 | 1 | 1 | 1 to 2 | 2 | 2 | 2 to 3 | 2 to 3 | 2 to 3 |
| 25 | 75 | 1 | 1 | 2 | 2 | 2 to 3 | 2 to 3 | 2 to 3 | 2 to 3 |
| 50 | 50 | 1 | 1 to 2 | 2 | 2 | 2 to 3 | 2 to 3 | 3 | 3 |
| 100 | 0 | 1 | 1 | 2 | 2 | 2 | 2 to 3 | 3 | 3 |
| \multicolumn{9}{c}{pH 7} | | | | | | | | |
| Blank | | 2 | 3 to 4 | 6 | 8 | N/A | N/A | N/A | N/A |
| 0 | 100 | 1 | 1 | 1 | 2 | 2 | 2 | 2 to 3 | 2 to 3 |
| 5 | 95 | 1 | 1 | 1 to 2 | 2 | 2 | 2 to 3 | 2 to 3 | 3 |
| 10 | 90 | 1 | 1 to 2 | 2 | 2 | 2 to 3 | 2 to 3 | 2 to 3 | 2 to 3 |
| 15 | 85 | 1 | 1 to 2 | 1 to 2 | 2 to 3 | 3 | 3 | 3 | 3 |
| 25 | 75 | 1 to 2 | 2 | 2 to 3 | 3 | 3 | 3 to 4 | 3 to 4 | 3 to 4 |
| 50 | 50 | 1 to 2 | 2 | 2 | 3 | 3 | 3 to 4 | 4 | 4 |
| 100 | 0 | 1 to 2 | 2 | 2 to 3 | 3 | 3 | 3 to 4 | 4 | 4 |
| \multicolumn{9}{c}{pH 9} | | | | | | | | |
| Blank | | 2 | 3 to 4 | 6 | 8 | N/A | N/A | N/A | N/A |
| 0 | 100 | 1 | 1 | 1 | 1 to 2 | 2 | 2 | 2 to 3 | 2 to 3 |
| 5 | 95 | 1 | 1 | 1 to 2 | 1 to 2 | 2 | 2 | 2 to 3 | 2 to 3 |
| 10 | 90 | 1 | 1 | 1 to 2 | 2 | 2 | 2 | 2 to 3 | 2 to 3 |
| 15 | 85 | 1 | 1 | 1 to 2 | 2 | 2 | 2 | 2 to 3 | 2 to 3 |
| 25 | 75 | 1 | 1 | 1 to 2 | 2 | 2 | 2 to 3 | 2 to 3 | 3 |
| 50 | 50 | 1 | 1 to 2 | 2 | 2 to 3 | 3 | 3 to 4 | 3 to 4 | 3 to 4 |
| 100 | 0 | 1 | 2 | 2 | 3 | 4 | 4 | 4 to 5 | 6 |
| \multicolumn{9}{c}{pH 12} | | | | | | | | |
| Blank | | 4 | 8 | 8 | N/A | N/A | N/A | N/A | N/A |
| 0 | 100 | 1 | 1 | 1 to 2 | 2 | 2 | 2 | 2 to 3 | 2 to 3 |
| 5 | 95 | 1 to 2 | 2 | 2 to 3 | 3 | 3 to 4 | 4 | 4 | 4 |
| 10 | 90 | 1 to 2 | 2 | 2 | 2 to 3 | 3 to 4 | 3 to 4 | 4 | 5 |
| 15 | 85 | 2 | 3 | 3 to 4 | 4 to 5 | 6 | 8 | 8 | N/A |
| 25 | 75 | 3 | 4 to 5 | 6 | 7 | 8 | N/A | N/A | N/A |
| 50 | 50 | 3 | 5 | 6 | 7 | 8 | N/A | N/A | N/A |
| 100 | 0 | 2 | 5 | 6 | 7 | 8 | N/A | N/A | N/A |

TABLE 3

Repulpability of Wax Coatings - 60° C.

| % H2 AKD | % Wax | \multicolumn{8}{c}{Repulping Time (Minutes)} | | | | | | | |
|---|---|---|---|---|---|---|---|---|---|
| | | 15 | 30 | 45 | 60 | 75 | 90 | 105 | 120 |
| \multicolumn{9}{c}{pH 5} | | | | | | | | |
| Blank | | 1 to 2 | 4 | 6 | 8 | N/A | N/A | N/A | N/A |
| 0 | 100 | 1 | 2 | 3 | 3 to 4 | 3 to 4 | 4 | 4 | 4 |
| 5 | 95 | 1 | 2 | 3 | 3 to 4 | 3 to 4 | 4 | 4 | 4 |
| 10 | 90 | 1 | 2 | 3 to 4 | 3 to 4 | 4 | 4 to 5 | 5 | 5 |
| 15 | 85 | 1 | 2 | 3 to 4 | 3 to 4 | 4 | 4 | 5 | 5 |
| 25 | 75 | 1 to 2 | 2 to 3 | 3 | 3 to 4 | 4 to 5 | 5 | 5 | 5 |
| 50 | 50 | 1 to 2 | 2 to 3 | 4 | 5 to 6 | 8 | N/A | N/A | N/A |
| 100 | 0 | 1 to 2 | 2 to 3 | 3 to 4 | 6 | 8 | N/A | N/A | N/A |
| \multicolumn{9}{c}{pH 7} | | | | | | | | |
| Blank | | 3 to 4 | 5 to 6 | 7 to 8 | 8 | N/A | N/A | N/A | N/A |
| 0 | 100 | 1 | 2 | 3 | 3 to 4 | 4 | 5 | 5 | 6 |
| 5 | 95 | 1 | 2 | 3 | 3 to 4 | 4 | 5 | 5 | 6 |
| 10 | 90 | 1 | 2 | 3 | 4 | 4 | 5 | 5 to 6 | 6 |
| 15 | 85 | 1 | 2 to 3 | 3 | 4 | 4 to 5 | 5 to 6 | 6 | 6 to 7 |
| 25 | 75 | 1 to 2 | 2 to 3 | 3 | 3 to 4 | 5 to 6 | 6 to 7 | 7 | 7 |
| 50 | 50 | 2 | 3 | 4 | 6 | 8 | N/A | N/A | N/A |
| 100 | 0 | 2 | 3 | 3 to 4 | 6 to 7 | 8 | N/A | N/A | N/A |
| \multicolumn{9}{c}{pH 9} | | | | | | | | |
| Blank | | 3 to 4 | 5 | 7 | 8 | N/A | N/A | N/A | N/A |
| 0 | 100 | 1 | 2 | 3 | 4 | 4 to 5 | 6 | 6 to 7 | 7 |
| 5 | 95 | 1 | 2 to 3 | 3 | 3 to 4 | 4 to 5 | 6 | 7 | 7 |
| 10 | 90 | 1 | 2 | 3 | 3 to 4 | 5 | 6 to 7 | 7 | 7 to 8 |

TABLE 3-continued

Repulpability of Wax Coatings - 60° C.

| % H2 AKD | % Wax | \multicolumn{8}{c}{Repulping Time (Minutes)} | | | | | | | |
|---|---|---|---|---|---|---|---|---|---|
| | | 15 | 30 | 45 | 60 | 75 | 90 | 105 | 120 |
| 15 | 85 | 1 | 2 | 3 | 4 | 5 | 6 to 7 | 7 | 7 to 8 |
| 25 | 75 | 2 | 3 | 4 | 4 | 5 | 6 | N/A | N/A |
| 50 | 50 | 2 to 3 | 5 to 6 | 7 to 8 | 8 | N/A | N/A | N/A | N/A |
| 100 | 0 | 2 to 3 | 5 to 6 | 7 to 8 | 8 | N/A | N/A | N/A | N/A |
| \multicolumn{10}{c}{pH 12} | | | | | | | | | |
| Blank | | 3 to 4 | 5 to 6 | 7 to 8 | 8 | N/A | N/A | N/A | N/A |
| 0 | 100 | 1 | 2 to 3 | 4 to 5 | 5 | 5 to 6 | 6 to 7 | 7 to 8 | 8 |
| 5 | 95 | 1 | 3 | 4 to 5 | 5 to 6 | 6 | 7 | 8 | N/A |
| 10 | 90 | 2 to 3 | 3 to 4 | 5 | 6 to 7 | 7 to 8 | 8 | N/A | N/A |
| 15 | 85 | 3 | 4 | 5 to 6 | 6 to 7 | 7 to 8 | 8 | N/A | N/A |
| 25 | 75 | 3 | 4 | 6 | 7 | 8 | N/A | N/A | N/A |
| 50 | 50 | 3 to 4 | 5 to 6 | 7 to 8 | 8 | N/A | N/A | N/A | N/A |
| 100 | 0 | 3 to 4 | 5 to 6 | 7 to 8 | 8 | N/A | N/A | N/A | N/A |

Example 6

Water Resistance of Various Wax/$H_2$-AKD Blends

Thirty (30) minute Cobb testing of the Paraflex®4797A, $H_2$-AKD, and Paraflex®4797A/$H_2$-AKD coated paperboard was carried out using Tappi method T441. The results are shown in Table 4. The unsized or uncoated paperboard gave little or no 30-minute Cobb sizing (value greater than 300 g/m$^2$). The paperboard coated with 100% Paraflex®4797A wax gave high levels of 30-minute Cobb sizing (Cobb sizing value less than 5 g/m$^2$, Cobb sizing value decreases as water resistance increases). Similar levels of Cobb sizing were maintained at $H_2$-AKD addition levels as high as 25% in Paraflex®4797A. The 50% and 100% $H_2$-AKD addition levels in Paraflex®4797A gave 30-minute Cobb sizing values between 15 and 35 g/m$^2$, a much higher level of sizing than the uncoated control sample.

MVTR testing of the Paraflex®4797A, $H_2$-AKD, and Paraflex®4797A/$H_2$-AKD coated paperboard was carried out using Tappi method T448. The testing was carried out at 23° C. and 85% relative humidity over a five day period. A saturated potassium bromide solution was used to control the humidity in the test chamber to 85%. The results are shown in Table 4. The MVTR results showed that the uncoated paperboard gave little or no resistance to moisture vapor transmission (MVTR greater than 500 g/m$^2$/day). Adding the 100% Paraflex®4797A coating reduced the moisture vapor transmission rate to less than 25 g/m$^2$/day. The Paraflex®4797A/$H_2$-AKD coated paperboard gave similar levels of moisture vapor resistance at $H_2$-AKD addition levels as high as 50%. The 100% $H_2$-AKD coated paperboard gave a slightly lower level of resistance to moisture vapor. The paperboard coated with 100% $H_2$-AKD had a higher moisture vapor resistance than the untreated paperboard.

The repulpability, Cobb sizing and MVTR results described in Examples 5 and 6 illustrate that adding $H_2$-AKD to a commercial wax coating improves the coated boards recyclability and repulpability while maintaining high levels of resistance to water and water vapor. Variations, modifications, and other implementations of what is described herein will occur to those of ordinary skill in the art without departing from the spirit and essential characteristics of the present teachings. Accordingly, the invention is intended to include all such modifications and implementations, and their equivalents.

Each reference cited in the present application, including books, patents, published applications, journal articles and other publications, is incorporated herein by reference in its entirety.

TABLE 4

Cobb Sizing and Moisture Vapor Transmission (MVTR) of Various Wax Coatings

| % $H_2$ Dimer | % Wax | 30 Minute Cobb Sizing (g/m$^2$) | MVTR (g/m$^2$/day) |
|---|---|---|---|
| Blank | | 300+ | 500 |
| 0% | 100% | 3.5 | 21 |
| 5% | 95% | 0.6 | 16 |
| 10% | 90% | 2.6 | 14 |
| 15% | 85% | 2.6 | 17 |
| 25% | 75% | 4.2 | 25 |
| 50% | 50% | 14.9 | 14 |
| 100% | 0% | 33.0 | 33 |

What is claimed is:

1. A composition comprising Formula I:

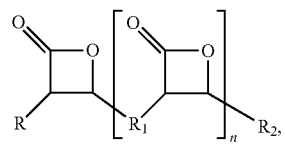

wherein
R is a branched or straight chain alkyl that is at least 6-carbon atoms in length; $R_1$ is a branched or straight chain alkyl containing from 2 to 34 carbon atoms; $R_2$ is a branched or straight chain alkyl that is at least 6-carbon atoms in length;
wherein
R, $R_1$ and $R_2$ may independently, optionally contain a cyclic functional group; and n is an integer from 1 to 6; and wherein Formula I is the result of the hydrogenation or partial hydrogenation of an alkyl ketene dimer, alkenyl ketene dimer, or ketene multimer.

2. The composition according to claim 1, wherein n is an integer from 0 to 3.

3. The composition according to claim 2, wherein n is 0.

4. The composition according to claim 1, wherein R and $R_2$ are from about 10 to about 22 carbons in length.

5. The composition according to claim 4, wherein R and $R_2$ is from about 10 to about 20 carbons in length.

6. The composition according to claim 5, wherein R and $R_2$ is from about 12 to about 18 carbons in length.

7. The composition according to claim 1, wherein the composition further comprises at least one additional wax.

8. The composition according to claim 7, wherein the at least one additional wax has a melting point of from about 30° C. to about 200° C.

9. The composition of claim 8, wherein the at least one additional wax has a melting point of from about 40° C. to about 85° C.

10. The composition according to claim 7, wherein the at least one additional wax is a paraffin wax or microcrystalline wax.

11. The composition of claim 1, wherein the composition optionally comprises a thermoplastic polymeric material, hydrocarbon resins, polyethylene acetate, polyethylene, or any combination thereof.

* * * * *